United States Patent
Kessler et al.

[11] Patent Number: 5,846,427
[45] Date of Patent: Dec. 8, 1998

[54] EXTRA-LUMENAL CROSSFLOW PLASMAPHERESIS DEVICES AND METHOD OF USE THEREOF

[75] Inventors: Stephen B. Kessler, Princeton; Sumith Ranil Wickramasinghe, Marlborough, both of Mass.

[73] Assignee: HemaSure, Inc., Marlborough, Mass.

[21] Appl. No.: 735,966

[22] Filed: Oct. 23, 1996

Related U.S. Application Data

[60] Provisional application No. 60/006,114, Oct. 23, 1995.
[51] Int. Cl.⁶ .......................... B01D 63/02; B01D 69/08
[52] U.S. Cl. ............... 210/645; 210/321.88; 210/500.23; 210/651
[58] Field of Search ................ 96/8, 10; 210/321.79, 210/321.8, 321.88, 321.89, 500.23, 645, 651, 646, 767

[56] References Cited

U.S. PATENT DOCUMENTS

| | | | |
|---|---|---|---|
| 3,228,877 | 1/1966 | Mahon | 210/500.23 |
| 3,342,729 | 9/1967 | Strand | 210/651 |
| 3,993,816 | 11/1976 | Baudet et al. | 210/500.23 |
| 4,995,967 | 2/1991 | Van Driessche | 210/500.23 |

*Primary Examiner*—Joseph W. Drodge
*Attorney, Agent, or Firm*—Bruce F. Jacobs

[57] ABSTRACT

Improved devices for blood separations are provided based on the use of hollow fiber membrane arrays in extra-lumenal crossflow filtration. Blood is processed extra-lumenally across an ordered array of microporous hollow fibers to separate cells from plasma. By use of extra-lumenal crossflow filtration with suitably oriented fibers, the separation device is more efficient than existing devices which benefits a patient or donor by reducing extracorporeal volume.

22 Claims, 2 Drawing Sheets

EXTRA-LUMENAL CROSSFLOW PLASMAPHERESIS DEVICES AND METHOD OF USE THEREOF

CROSS REFERENCE TO RELATED APPLICATION

This application claims the benefit of U.S. Provisional Application No. 60/006,114 filed Oct. 23, 1995.

BACKGROUND OF THE INVENTION

The present invention relates to plasmapheresis, i.e. removal of plasma from blood, which is currently performed in continuous flow centrifugal separators, which separate cells by density; flat-sheet and intra-lumenal hollow fiber membrane devices, which operate by tangential flow microfiltration; and rotating membrane devices, which enhance microfiltration flux by inducing Taylor vortices. Although useful, each of these devices has its own inadequacies due to one or more of complexity, energy demand, inability to function with simple pumps or under gravity flow, required time for plasma separation, require an undesirably large extracorporeal volume, and the like.

Hollow-fiber membranes have been used for plasmapheresis by means of intra-lumenal flow in which a cell-containing liquid is introduced within the lumens of the hollow fibers and a cell-free liquid passes through the membrane as permeate. Such intra-lumenal flow cell separation devices have been reviewed in the literature: c.f. *Plasmapheresis: Therapeutic Applications and New Techniques*, Nosé Y, et al., Raven Press, New York (1983); Kessler S. B., *Blood Purif.*, 11:150–157 (1993); and U.S. Pat. Nos. 4,243,532, 4,609,461, 4,668,399 and 4,729,829. These devices require the use of large amounts of fiber, typically more than 1,000 sq. cm. of fiber area, have high energy demands, and do not usually function under simple gravity flow. Thus benefits from using hollow fiber membranes have been below expectations.

The use of hollow-fiber membranes to remove particles from a solution by extra-lumenal flow is known. In general extra-lumenal flow, a feed, i.e. a particle-containing liquid, enters from the shell side of a module and flows across the hollow fiber membranes so that a particle-free liquid passes into the fiber lumens as permeate. Extra-lumenal flow is generally associated with higher Reynolds numbers than intra-lumenal flow (at equal energy consumption per unit membrane area) and therefore leads to a decrease in the accumulation of rejected species. This accumulation is further disrupted by the discontinuous nature of the filtration surface in the direction of flow. These combined effects often lead to enhanced mass transfer in extralumenal flow devices. U.S. Pat. No. 3,993,816, perhaps the earliest reference to extra-lumenal, hollow-fiber filtration utilized rectangular arrays of hollow fibers. A similar fabrication technique and resulting module is described in U.S. Pat. No. 4,959,152. The filtration of latex particles and yeast by extra-lumenal flow hollow fiber devices has been described: Knops F N M, *J. Membrane Sci.*, 73:153–161 (1992). The devices used were produced by stacking single-layer parallel arrays of hollow fibers, alternating the direction of the fibers in each layer, and sealing the ends by centrifugal encapsulation. The resulting modules have hollow fiber membranes disposed perpendicular to the axis of the cylinder in which the lumens terminated on the surface of the cylinder.

Prior art extra-lumenal flow devices have been found unsuitable for the filtration of blood for a variety of reasons. They have required a high extra-lumenal flow rate per unit membrane area and/or recirculation to successfully effect the filtrations. Red blood cells are quite fragile and undergo gross hemolysis if treated too aggressively. Therefore blood is not suitable for any processing which utilizes high extra-lumenal flow rates and recirculation of extra-lumenal flow is undesirable.

Additionally, many prior art devices utilized membranes that were partially skinned with low surface porosity and reduced hydraulic permeability. While these membranes can be used effectively to process feedstocks containing rigid, non-deformable particles, e.g. yeast particles, which cannot enter small membrane pores, they are not suitable for processing whole blood. Attempts to use a module designed for the extra-lumenal processing of yeast particles with human blood were unsuccessful. When tested with blood, the blood exhibited gross hemolysis and under constant flux operation, the transmembrane pressure drop was excessively high due to membrane fouling. The module, with widely spaced fibers and an average packing density of 15–20%, required high extra-lumenal flow rates to achieve acceptably high average wall shear rates. However, the high flow rates resulted in excessively high maximum wall shear rates and shear stresses upon the formed elements of the blood sample. In addition, the membrane had low surface porosity, requiring high transmembrane pressure to achieve adequate fluxes.

Although hollow fiber devices which use extra-lumenal blood flow have been developed, they have been limited to the field of blood oxygenation. Blood oxygenators effect gas/liquid transfer, i.e. oxygen into blood, while specifically excluding liquid permeation (filtration) into hollow fiber membranes as is the basis of the present invention. In blood oxygenators any filtration is precluded by use of hydrophobic hollow fiber membranes having small pores and by operating at liquid-side pressures that are below the intrusion pressure of the membrane.

Accordingly, it is an object of this invention to produce an improved blood separation device and method for separating blood cells which uses extra-lumenal crossflow filtration.

It is a further object to produce a device suitable for use in donor plasmapharesis which device can be operated with only peristaltic pumps or, preferably, by gravity flow alone and which use less than about 500 sq cm of external hollow fiber surface area.

It is a further object to produce an extra-lumenal blood filtration device which causes minimal hemolysis of red blood cells processed therewith.

It is a further object to produce an extra-lumenal blood filtration device which is sufficiently effective that it can operate in single pass mode, i.e. without requiring blood recirculation to obtain a satisfactory separation.

It is a further object to produce extra-lumenal filtration devices which function at the flow rate by which blood normally exits a donor's body.

These and still further objects will be apparent from the detailed disclosure which follows.

DISCLOSURE OF THE INVENTION

The present invention is directed to the production of improved devices using hollow-fiber membrane arrays to perform blood separations. More particularly, the devices are based upon extra-lumenal crossflow filtration wherein blood is introduced extralumenally and caused to flow across an array of microporous hollow fiber membranes. The hollow fiber membranes are oriented both with respect to each other and to the flow of the blood so as to minimize red blood cell hemolysis and deposition onto the membranes.

DETAILED DESCRIPTION OF THE PREFERRED EMBODIMENTS

Figure 1A:
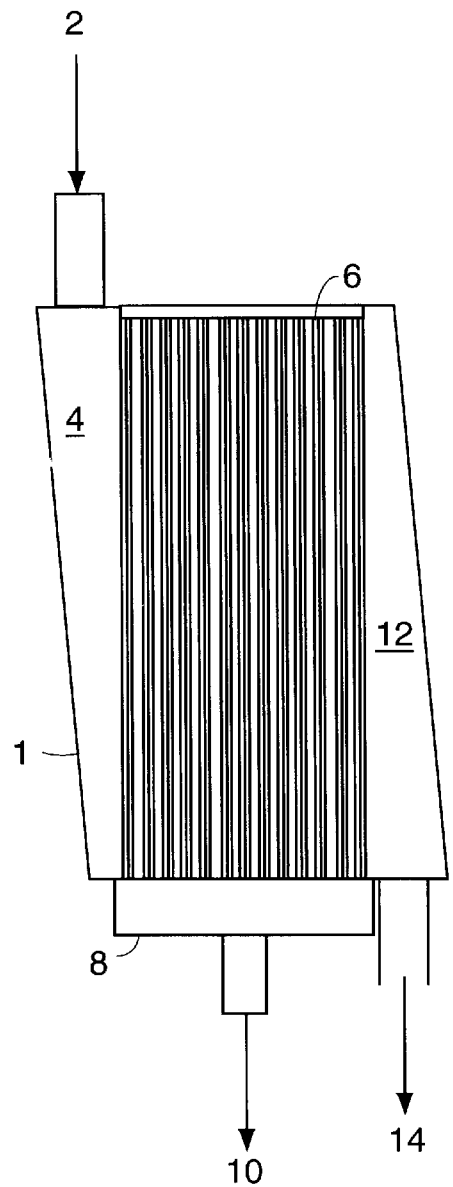
FIG. 1A is a view along the centerline of a device of this invention showing the hollow fiber array and the flows of blood cells and liquid through it.
Figure 1B:
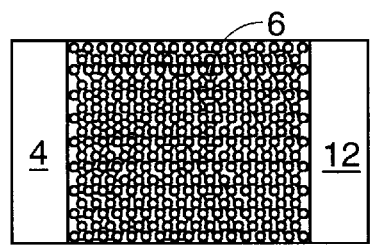
FIG. 1B is a cross-sectional view of the device of FIG. 1A.

The devices of this invention are useful in separating blood cells from a liquid in which they are suspended. Generally the liquid will be plasma and the cells will be separated from whole blood. Alternatively, a liquid suspension of blood cells may be used. The devices operate by flowing the cell suspension over the external surfaces of hollow-fiber membranes in an operation referred to herein as "extra-lumenal crossflow" (XLC) filtration. In an XLC filtration device 1, as shown in FIGS. 1A and 1B, a cell-containing liquid 2 is shell side fed through in inlet manifold 4 into and across a hollow fiber array 6 containing individual hollow fiber membranes 7 (best seen in FIG. 2). When the cell-containing liquid flows around and across the outside of the individual hollow fiber membranes 7 in the array 6, a portion of that liquid flows through the porous walls of an individual hollow fiber and into each fiber lumen 9. The liquid in the fiber lumens 9 exits the hollow fibers 7 into a liquid outlet manifold 8. The blood cells which do not enter the fiber lumens are collected in a shell-side outlet manifold 12 and exit the device 1 in the form of a concentrated cell suspension 14.

"Crossflow" is used herein to refer to flow wherein the net direction of flow crosses the axes of the hollow fibers. Thus the flow is at an angle to the fibers of from greater than 0° up to 90°, preferably about 10° to 90°, and more preferably about 40° to 90°. Crossflow is contrasted with "tangential flow" in which the flow which is only parallel to the direction of the hollow fibers.

Like other filtrations, XLC blood filtration can be characterized by a rate-limiting flux. In the case of XLC blood filtration, the value of the rate-limiting flux is determined principally by a concentration boundary layer of blood cells which accumulate at the membrane surfaces. Unlike many other filtration processes, fouling of a membrane is negligible in a properly controlled blood filtration process and the rate-limiting flux tends to be time-independent within the time scale of typical processes. It has been discovered that the value of the limiting flux depends instead upon the hollow fibers, their orientation and packing density within the device, and the direction of flow with respect to the hollow fibers.

The values of the rate-limiting flux for preferred embodiments of this invention substantially exceed the rate-limiting fluxes achieved by tangential flow intra-lumenal plasmapheresis devices at similar conditions. The higher fluxes allow a much smaller device to process the same volume of blood per unit time or allow a device of equal size to process a larger volume of blood per unit time. Smaller devices can benefit the patient or donor by reducing extracorporeal volume and can be made at lower cost. Processing a given volume of blood in less time provides another benefit to patient or donor.

To obtain effective XLC filtration of blood in accordance with the present invention, certain aspects of the geometry of the hollow-fiber array, dimensions of the fibers, means of spacing the fibers, membrane morphology, and the relationship of these geometric factors to specific operating parameters, of blood flow rate and filtration rate, should be controlled. The present invention will now be described in terms of these factors.

Suitable hollow fiber membranes useful in XLC blood filtration devices have an area-average surface pore size, as characterized by scanning electron microscopy, of about 8 $\mu$m or less, preferably less than 3 $\mu$m. By porometry or bubble point test, the average pore size should be between about 0.1 and 1 $\mu$m. If no macromolecules are present in the suspending liquid (e.g. after deglycerolization of previously frozen blood), then the lower limit on membrane pore size only affects the filtration rate. If macromolecules are to be removed with the filtrate (e.g. during donor plasmapheresis), then a lower limit on average pore size of about 0.1 $\mu$m is applicable. The fibers themselves may be isotropic or anisotropic in their morphology. The hollow fibers generally have an outside diameter of between about 100 $\mu$m and 1,500 $\mu$m and an inside diameter of about 50 to 1,200 $\mu$m. The hollow fibers may be produced from any material which does not adversely affect both the blood cells and the suspending liquid. Suitable such materials are those used in current intra-lumenal blood filtration and include: polysulfone, cellulose acetate, polypropylene, polyvinylidene difluoride, polyether sulfone, polyvinyl alcohol, polymethylmethacrylate, and the like.

Figure 2:
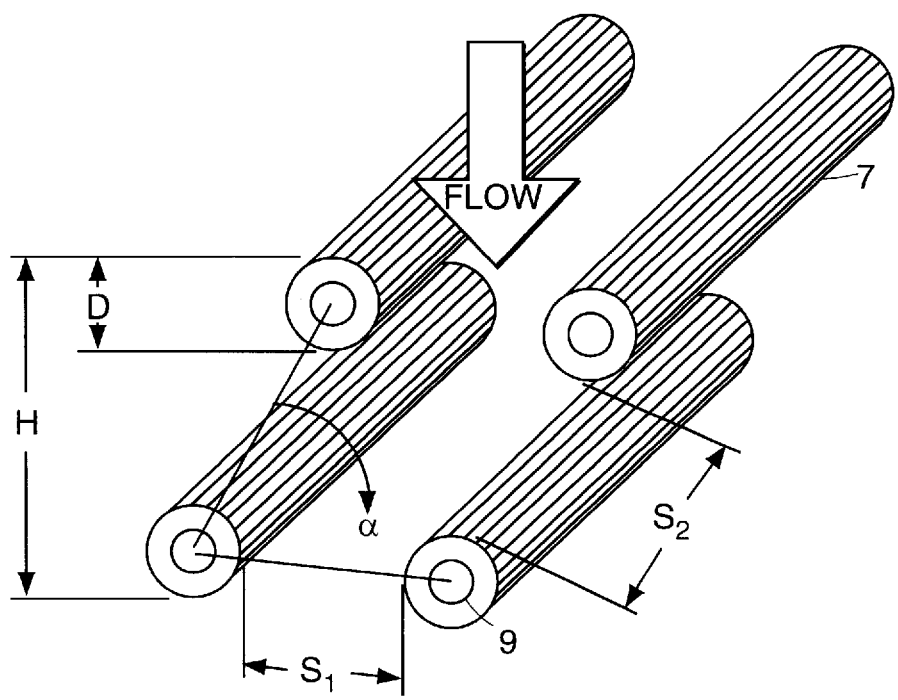
FIG. 2 is a perspective view of an embodiment of this invention in which the orientation of four hollow fiber membranes with respect to each other is shown.

The individual hollow fibers are formed into an array which is characterized by (i) a void fraction $\epsilon$, (ii) an overall bed depth H, (iii) transverse and longitudinal fiber spacings $S_1$ and $S_2$, and (iv) an angle $\alpha$ of off-set from one row to the next as shown in FIG. 2.

For effective XLC blood filtration devices, the void fraction is between about 0.2 and 0.8, preferably between about 0.4 and 0.6. The void fraction corresponds to a fiber packing density of about 20 to 80%, preferrably 40 to 60%. The packing density for a perfectly packed hexagonal array of hollow fibers is about 91%.

Overall bed depth is also an important parameter as it affects both the uniformity of flow across the hollow fiber array and the pressure drop across the array, which, in turn, affects the transmembrane pressure. The overall bed depth is about 0.5 to 20 cm, preferably about 1 to 5 cm. While bed depths outside of this range can be used, they are not recommended.

The average fiber spacing will be determined by the fiber outside diameter and selected void fraction. The uniformity of fiber spacing should be controlled so as to prevent poor flow distribution and channeling. As shown in FIG. 2 for a regular array of hollow fibers 7, $S_1$ is the horizontal distance between two adjacent fibers and $S_2$ is the vertical distance between two adjacent fibers. The average ratio $S_1/S_2$ has a value of about 0.5 to 2.0, preferably about 0.8 to 1.5. The range of variation of $S_1$ and $S_2$ between each pair of adjacent fibers is preferably limited to ±50% with respect to the average values. $\alpha$, the angle of offset between adjacent rows of fibers in regular arrays, is between about 15° and 75°, preferably between about 30° and 60°.

Alternatively, random fiber arrays may also be used provided that they meet the void fraction and overall bed depth described herein.

In addition to the above-defined ranges, relationships among some of the parameters must also be controlled to assure stable operating conditions. Leukocytes and platelets have been shown to exhibit functional impairment due to shear stresses imparted in laminar flow fields at shear rates above a limiting value. For whole blood this limiting value of shear rate is about 3,000 sec$^{-1}$. To ensure a safe operating range with respect to the leukocytes and platelets, a maximum value of wall shear rate $\gamma_{W,WMAX}$ of about 2,000 sec$^{-1}$ should be observed in design of the device and in selection of operating conditions. This results in a limitation on the maximum pressure drop $\Delta P_{A1}$ allowable across the fiber array as defined in Equation 1:

$$\Delta P_{A1} = \gamma_{W,MAX} \cdot \mu \cdot A_W / A_C$$

wherein $\gamma_{W,MAX}$ is the maximum design wall shear rate;
$\mu$ is the viscosity of the blood;
$A_W$ is the total external wetted area of the hollow fibers; and
$A_C$ is the total cross-sectional area of the fiber array normal to flow.

Another factor that must be considered is the tendency of erythrocytes (red blood cells) to hemolyze if they are extruded into membrane pores at high transmembrane pressures. This effect is a function of membrane pore size, transmembrane pressure and wall shear rate. The extent of hemolysis is inversely proportional to wall shear rate $\gamma_W$; thus maximizing the value of $\gamma_W$ is beneficial in avoiding hemolysis. The membrane pore size which pertains here is the surface pore size as determined by scanning electon microscopy. For a value of $\gamma_{W,MAX}$ of 2,000 sec$^{-1}$, the value of the critical pressure function $\Delta P_{TM,MAX}$ that will avoid significant hemolysis, according to FIG. 5 of Zydney et al, *Chem. Eng. Commun.*, 30:191–207 (1984), times the pore radius $R_P$ of the membrane equals about 100 mm Hg•$\mu$m. Thus for a membrane of area-average surface pore diameter 2 $\mu$m, $R_P$ of 1 $\mu$m, $\Delta P_{TM,MAX}$ is $100/R_P$, which equals 100 mm Hg.

This limitation on $\Delta P_{TM,MAX}$ places a second limit on the maximum pressure drop allowable across the fiber array $\Delta P_{A2}$ as defined in Equation 2:

$$\Delta P_{A2} = \Delta P_{TM,INLET} - \Delta P_{TM,OUTLET} = \Delta P_{TM,MAX} - \Delta P_{TM,OUTLET}$$

Thus for effective rapid XLC without damage to the cells, $\Delta P_A$ must be limited to the smaller of the two values defined by Equations 1 and 2. If $\Delta P_{A1}$ is greater than $\Delta P_{A2}$, then the value of $A_C$ can be adjusted such that $\Delta P_{A1}$ equals $\Delta P_{A2}$. If $\Delta P_{A2}$ is greater than $\Delta P_{A1}$, then $\Delta P_{TM,INLET}$ can be lowered such that $\Delta P_{A2}$ equals $\Delta P_{A1}$.

Initial values of $\Delta P_{TM,INLET}$ and $A_W$ are estimated based on the required permeate flow rate for the application and the properties of the membrane, in particular its pore size and permeability. Experimentation can fine tune these estimates for specific XLC filtration systems and Equations 1 and 2 applied iteratively to arrive at final preferred design parameters for a specific fiber array.

Once the design parameters of the fiber array are determined, construction of the array can be carried out by any of a number of techniques well known in the art. For example, a fabric can be created by knitting or weaving hollow fibers with a filler yarn or monofilament. The fabric can then be cut and stacked or folded to form the desired array. An alternate method is to pass fibers through a series of grids, thus forming a three-dimensional array. Double-sided, pressure sensitive tape can be employed to secure fibers relative to each other in the same plane and then to bond layer to layer. A particularly preferred method is to use hot melt adhesives applied either as a molten bead or as a monofilament which is subsequently melted. Once formed, the methods for enclosing a fiber array in a housing are well known to those skilled in the art and thus further details are not included herein. The overall device configuration may be rectangular, cylindrical or any other shape.

The blood flow into the XLC device when used for donor plasmapheresis is generally at a rate of about 50 to 100 cc/mm and the total external surface area of the hollow fibers is less than 500 sq. cm., preferably less than 300 sq. cm., and most preferably less than 200 sq. cm.

EXAMPLE

A hollow fiber array is constructed from 190 polyether sulfone hollow fiber membranes having an outside diameter of 1,000 $\mu$m, an inside diameter of 600 $\mu$m, a length of 4 cm, an area-average surface pore size of 3 $\mu$m (estimated by scanning electron microscopy), an average pore size of 0.5 $\mu$m (determined by porometry), and a surface porosity of 60–70% (estimated by scanning electron microscopy). The total external surface area of the hollow fibers is 240 sq. cm.

A random array having a width of 2 cm, a depth of 1.5 cm, a packing density of 50%, and an effective fiber length of 4 cm after encapsulation, is formed by placing the hollow fibers into a polycarbonate housing. Using a two-component polyurethane, the ends of the array are encapsulated and bonded to the housing. The tips of the hollow fibers at what will be the outlet end of the array are cut off and manifolds attached to form the XLC device shown in FIGS. 1A and 1B.

The device is tested with a suspension of fresh (less than 24 hours old), microaggregate-filtered, human whole blood and the blood hematocrit is raised from about 40 to more than 60, i.e. the plasma content has been reduced from 60% to 40%.

What is claimed is:

1. A device for separating blood cells from a liquid in which the cells are suspended which comprises a microporous hollow fiber membrane array disposed within a casing, the membrane array having (i) an average ratio $S_1/S_2$ of about 0.5 to 2.0, $S_1$ being a horizontal distance between the fibers, $S_2$ being a vertical distance between two adjacent fibers, (ii) a void fraction of about 0.2 and 0.8, (iii) an overall depth of about 0.5 to 20 cm, and (iv) an angle of offset, $\alpha$, between two adjacent rows of the hollow fibers that is between 15° and 75°, a liquid and blood cell inlet disposed on one side of said casing, a liquid outlet fed solely by the hollow fibers, and a concentrated liquid and blood cell outlet disposed on an opposite side of said casing from said inlet, wherein the liquid in which the cells are suspended flows across the hollow fiber membrane array.

2. The device of claim 1, wherein the liquid comprises plasma and the blood cells are separated from the plasma.

3. The device of claim 1, wherein the hollow fiber membranes have an area-average surface pore size, as determined by scanning electron microscopy, of about 8 $\mu$m or less.

4. The device of claim 1, wherein the hollow fiber membranes have an average pore size of about 0.1 to 1 $\mu$m, as determined by porometry.

5. The device of claim 1, wherein the hollow fibers have an isotropic morphology.

6. The device of claim 1, wherein the hollow fibers have an anisotropic morphology.

7. The device of claim 1, wherein the hollow fibers have an outside diameter of between about 100 $\mu$m and 1,500 $\mu$m and an inside diameter of about 50 to 1,200 $\mu$m.

8. The device of claim 1, wherein the hollow fibers are prepared from a polymer selected from the group consisting of polysulfone, cellulose acetate, polypropylene, polyvinylidene difluoride, polyether sulfone, polyvinyl alcohol, and polymethylmethacrylate.

9. The device of claim 1, wherein the hollow fiber array has an overall depth of about 0.5 to 20 cm.

10. The device of claim 1, wherein the range of variation of $S_1$ and $S_2$ between each pair of adjacent fibers is ±50% with respect to their average values.

11. The device of claim 1, wherein $\alpha$, the angle of offset between two adjacent rows of hollow fibers, is between about 30° and 60°.

12. The device of claim 1, wherein the hollow fiber array is a random array.

13. The device of claim 1, wherein the total external surface area of the hollow fiber membranes is less than 500 sq. cm.

14. A method for removing blood cells from a blood cell-containing liquid which comprises passing the liquid extra-lumenally across an array of hollow fiber microporous membranes having a spacing of fibers, a void fraction and an arrangement of fibers into offset rows configured for facilitating effective separation of blood cells from liquid.

15. The method of claim 14, wherein the blood cell containing liquid is human whole blood.

16. The method of claim 14, wherein the passing of the liquid is performed at a maximum membrane wall shear rate of about 2,000 $\sec^{-1}$.

17. The method of claim 14, wherein the maximum pressure drop across the hollow fiber array is 2,000 $\sec^{-1} \cdot \mu \cdot A_W / A_C$ wherein $\mu$ is the viscosity of the blood cell containing liquid; $A_W$ is the total external wetted area of the hollow fibers; and $A_C$ is the total cross-sectional area of the fiber array normal to flow.

18. The method of claim 14, wherein the hollow fiber membranes have an area-average surface pore size, as determined by scanning electron microscopy, of about 8 $\mu$m or less; an average pore size of about 0.1 to 1 $\mu$m, as determined by porometry; an outside diameter of between about 100 $\mu$m and 1,500 $\mu$m and an inside diameter of about 50 to 1,200 $\mu$m.

19. The method of claim 14, wherein the array is a random array.

20. The method of claim 14, wherein the array is a regular array.

21. The method of claim 20, wherein $S_1$ is the horizontal distance between two adjacent fibers, $S_2$ is the vertical distance between two adjacent fibers, the average ratio $S_1/S_2$ is about 0.5 to 2.0, and $\alpha$, the angle of offset between two adjacent rows of hollow fibers, is between about 15° and 75°.

22. The method of claim 21, wherein the range of variation of $S_1$ and $S_2$ between each pair of adjacent fibers is ±50% with respect to their average values.

* * * * *